US008367847B2

(12) United States Patent
Buddoo et al.

(10) Patent No.: US 8,367,847 B2
(45) Date of Patent: Feb. 5, 2013

(54) PRODUCTION OF MONATIN ENANTIOMERS

(75) Inventors: Subash Buddoo, Randburg (ZA); Amanda Louise Rousseau, Bedford Gardens (ZA); Gregory E. R. Gordon, Melville (ZA)

(73) Assignee: Cargill, Incorporated, Wayzata, MN (US)

( * ) Notice: Subject to any disclaimer, the term of this patent is extended or adjusted under 35 U.S.C. 154(b) by 1008 days.

(21) Appl. No.: 11/865,441

(22) Filed: Oct. 1, 2007

(65) Prior Publication Data

US 2009/0088577 A1    Apr. 2, 2009

(51) Int. Cl.
C07D 209/08    (2006.01)
(52) U.S. Cl. .......................... 548/502; 548/494
(58) Field of Classification Search ................ None
See application file for complete search history.

(56) References Cited

U.S. PATENT DOCUMENTS

| | | | |
|---|---|---|---|
| 3,002,889 A | 10/1961 | Kinoshita et al. | |
| 3,751,458 A | 8/1973 | Wiley | |
| 3,936,472 A | 2/1976 | Kinney et al. | |
| 4,010,204 A | 3/1977 | Koster et al. | |
| 4,975,298 A | 12/1990 | Van Wyk et al. | |
| 5,128,164 A | 7/1992 | Van Wyk et al. | |
| 5,128,482 A | 7/1992 | Olivier et al. | |
| 5,545,644 A | 8/1996 | Macor et al. | |
| 5,703,270 A | 12/1997 | Nakagawa et al. | |
| 5,994,559 A | 11/1999 | Abushanab et al. | |
| 6,218,167 B1 | 4/2001 | Allen et al. | |
| 6,264,999 B1 | 7/2001 | Yatka et al. | |
| 6,277,626 B1 | 8/2001 | Hansen et al. | |
| 6,489,100 B1 | 12/2002 | Liao | |
| 6,743,910 B2 | 6/2004 | Cimpola et al. | |
| 7,064,219 B2 | 6/2006 | Kawahara et al. | |
| 7,081,359 B2 | 7/2006 | Lim | |
| 7,354,746 B1 | 4/2008 | Suzuki et al. | |
| 7,390,909 B2 * | 6/2008 | Kawahara et al. | ............ 548/495 |
| 7,396,941 B2 | 7/2008 | Mori et al. | |
| 7,534,898 B2 | 5/2009 | Amino et al. | |
| 7,781,005 B2 | 8/2010 | Mori | |
| 7,816,541 B2 | 10/2010 | Kawahara et al. | |
| 7,888,081 B2 | 2/2011 | Khare et al. | |
| 8,003,361 B2 | 8/2011 | Brady et al. | |
| 2003/0228403 A1 | 12/2003 | Amino et al. | |
| 2004/0063175 A1 | 4/2004 | Abraham et al. | |
| 2005/0004394 A1 | 1/2005 | Kawahara et al. | |
| 2005/0009153 A1 | 1/2005 | Sugiyama et al. | |
| 2005/0020508 A1 | 1/2005 | Amino et al. | |
| 2005/0106305 A1 | 5/2005 | Abraham et al. | |
| 2005/0112260 A1 | 5/2005 | Abraham et al. | |
| 2005/0118317 A1 | 6/2005 | Amino et al. | |
| 2005/0137246 A1 | 6/2005 | Amino et al. | |
| 2005/0153405 A1 | 7/2005 | Sugiyama et al. | |
| 2005/0170041 A1 | 8/2005 | Abraham et al. | |
| 2005/0221453 A1 | 10/2005 | Takagi et al. | |
| 2005/0221455 A1 | 10/2005 | McFarlan et al. | |
| 2005/0244937 A1 | 11/2005 | Abraham et al. | |
| 2005/0244939 A1 | 11/2005 | Sugiyama et al. | |
| 2005/0272939 A1 | 12/2005 | Amino et al. | |
| 2005/0282260 A1 | 12/2005 | Hicks et al. | |
| 2006/0003411 A1 | 1/2006 | Sugiyama et al. | |
| 2006/0003426 A1 | 1/2006 | Sugiyama et al. | |
| 2006/0009394 A1 | 1/2006 | Amino | |
| 2006/0014819 A1 | 1/2006 | Mori et al. | |
| 2006/0074249 A1 | 4/2006 | Kawahara et al. | |
| 2006/0083695 A1 | 4/2006 | Mori | |
| 2006/0154343 A1 | 7/2006 | Mori et al. | |
| 2006/0172396 A1 | 8/2006 | Sugiyama et al. | |
| 2006/0252135 A1 | 11/2006 | Brazeau et al. | |
| 2007/0099277 A1 | 5/2007 | Anderson et al. | |
| 2007/0105938 A1 | 5/2007 | Anderson et al. | |
| 2008/0020434 A1 | 1/2008 | Brazeau et al. | |
| 2008/0020435 A1 | 1/2008 | Burke et al. | |
| 2008/0274518 A1 | 11/2008 | Hicks et al. | |
| 2009/0087829 A1 | 4/2009 | Brady et al. | |
| 2009/0087888 A1 | 4/2009 | Buddoo et al. | |
| 2009/0117625 A1 | 5/2009 | Abraham et al. | |
| 2009/0130285 A1 | 5/2009 | Abraham et al. | |
| 2009/0198072 A1 | 8/2009 | Khare et al. | |
| 2009/0259052 A1 * | 10/2009 | Kawahara et al. | ............ 548/502 |
| 2010/0221795 A1 | 9/2010 | Takakura et al. | |
| 2011/0020882 A1 | 1/2011 | de Souza et al. | |
| 2011/0045547 A1 | 2/2011 | de Souza et al. | |
| 2011/0300282 A1 | 12/2011 | Brady et al. | |
| 2012/0009634 A1 | 1/2012 | Burke et al. | |

FOREIGN PATENT DOCUMENTS

| | | |
|---|---|---|
| EP | 0 438 314 | 4/1994 |
| EP | 1 045 029 | 10/2000 |
| EP | 1 350 791 | 10/2003 |
| EP | 1 445 323 | 8/2004 |
| EP | 1 449 832 | 8/2004 |
| EP | 1 533 376 | 5/2005 |
| EP | 1 580 268 | 9/2005 |
| EP | 1 605 041 | 12/2005 |
| EP | 1 719 758 | 11/2006 |
| JP | 2002-060382 | 2/2002 |
| JP | 2003-171365 | 6/2003 |

(Continued)

OTHER PUBLICATIONS

Curran, Dennis P., "Reduction of DELTA.2.Isoxazolines: A Conceptually Different Approach to the Formation of Aldol Adducts", Journal of the American Chemical Society, 104, 4024-4026, 1982.*
Ackerman, "Structure elucidation of and synthetic approaches to monatin, a metabolite from schlerochiton ilicifolius," PhD dissertation, University of Stellenbosch, Jul. 1990.
Ager et al., "Commercial, Synthetic Nonnutritive Sweeteners," *Agnew. Chem. Int. Ed.*, 1998, 37:1802-1817.
Ager et al., "Novel biosynthetic routes to non-proteinogenic amino acids as chiral pharmaceutical intermediates," *Journal of Molecular Catalysis B: Enzymatic*, 2001, 11:199-205.
Azuma et al., "Hyper-production of L-tryptophan via fermentation with crystallization," *Appl. Microbiol. Biotechnol.*, 1993, 39:471-476.

(Continued)

Primary Examiner — Fiona T Powers

(57) ABSTRACT

Methods for the preparation of the high intensity sweetener, monatin, 3-(1-amino-1,3-dicarboxy-3-hydroxy-but-4-yl)indole, its salts and internal condensation products thereof, including methods applicable to the large-scale production of monatin are described.

12 Claims, 7 Drawing Sheets

FOREIGN PATENT DOCUMENTS

| | | |
|---|---|---|
| JP | 2004-222657 | 8/2004 |
| JP | 2004-331644 | 11/2004 |
| JP | 2004-331650 | 11/2004 |
| WO | WO 89/11212 | 11/1989 |
| WO | WO 03/045914 | 6/2003 |
| WO | WO 03/056026 | 7/2003 |
| WO | WO 03/059865 | 7/2003 |
| WO | WO 03/091396 | 11/2003 |
| WO | WO 2005/001105 | 1/2005 |
| WO | WO 2005/014839 | 2/2005 |
| WO | WO 2005/016022 | 2/2005 |
| WO | WO 2005/020721 | 3/2005 |
| WO | WO 2005/042756 | 5/2005 |
| WO | WO 2005/082850 | 9/2005 |
| WO | WO 2006/011613 | 2/2006 |
| WO | WO 2006/113897 | 10/2006 |
| WO | WO 2006/116487 | 11/2006 |
| WO | WO 2007/103389 | 9/2007 |
| WO | WO 2007/133183 | 11/2007 |
| WO | WO 2007/133184 | 11/2007 |
| WO | WO2010/105014 | 9/2010 |
| WO | WO2010/138513 | 12/2010 |
| WO | WO2011/082351 | 7/2011 |
| WO | WO2011/082353 | 7/2011 |
| WO | WO2011/082363 | 7/2011 |
| WO | WO2011/082365 | 7/2011 |

OTHER PUBLICATIONS

Bae et al., "Production of aromatic D-amino acids from α-keto acids and ammonia by coupling of four enzyme reactions," *Journal of Molecular Catalysis B: Enzymatic*, 1999, 6:241-247.

Bassoli, "'Chemistry-Nature,' still an open match for the discovery of new intensive sweeteners," *Agro Food industry hi-tech*, 2004, 15(4):27-29.

Bassoli et al., "Design and synthesis of new monatin derivatives," *Abstracts, 13th International Symposium on Olfaction and Taste (ISOT XIII), 14th. European European Chemoreception Research Organization Congress (ECRO XIV)*, Jul. 20-24, 2000, p. 162.

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of *Neisseria gonorrhoeae*: Ties to Aromatic Metabolism," *J. Gen. Microbiol.*, 1989, 135:353-360.

Bommarius et al., "Some new developments in reductive amination with cofactor regeneration," *Biocatalysis*, 1994, 10:37-47.

Bongaerts et al., "Metabolic Engineering for Microbial Production of Aromatic Amino Acids and Derived Compounds," *Metabolic Engineering*, 2001, 3:289-300.

Brandl and Lindow, "Cloning and characterization of a locus encoding an indolepyruvate decarboxylase involved in indole-3-acetic acid synthesis in *Erwinia herbicola*," *Appl. Environ. Microbiol.*, 1996, 62:4121-4128.

Camargo (Ediclea Cristina Fregonese Camargo), "Preparation of amino acids not proteinogênicos, structurally related to adoçante natural Monatina" [translated by Google], Jan. 2003, Universidade Estadual de Campinas Instituto de Quimica, Dissertation of Masters.

Curran, "Reduction of .DELTA.2-isoxazolines: a conceptually different approach to the formation of aldol adducts," *J. Am. Chem. Soc.*, 1982, 104:4024-4026.

DeLuna et al., "NADP-Glutamate Dehydrogenase Isoenzymes of *Saccharomyces cerevisiae*: Purification, Kinetic Properties, and Physiological Roles," *J. Biol. Chem.*, 2001, 276(47):43775-43783.

Floyd et al., "A Simple Strategy for obtaining both Enantiomers from an Aldolase Reaction: Preparation of L- and D-4-Hydroxy-2-ketoglutarate," *J. Chem. Soc. Perkin Trans. 1*, 1992, 1085-1086.

Henderson et al., "Stereospecific Preparation of the N-Terminal Amino Acid Moiety of Nikkomycins KX and KZ via a Multiple Enzyme Synthesis," *J. Org. Chem.*, 1997, 62:7910-7911.

Holzapfel et al., "A simple cycloaddition approach to a racemase of the natural sweetener monatin," *Synthetic Communications*, 1994, 24(22):3197-3211.

Holzapfel et al., "The synthesis of a gamma-keto-alpha-amino acid, a key intermediate in the synthesis of monatin, a new natural sweetener," *Synthetic Communications*, 1993, 23(18):2511-2526.

Izumi, "Introduction," *Synthetic Production and Utilization of Amino Acids*, 1974, Kankeko et al.(eds.), Halstad Press, Chapter 1, pp. 3-16.

Juhl et al., "Catalytic asymmetric homo-aldol reaction of pyruvate—a chiral Lewis acid catalyst that mimics aldolase enzymes," *Chem. Commun.*, 2000, 2211-2212.

Kogiso et al., "Control of Lactamization during the Synthesis of the Monatin Analogue," *Peptide Science*, 2003, pp. 195-198.

Kogiso et al., "The C-C Bond Formation with Alkyl Halide in Monatin Analogue Synthesis and Their Tastes Expression," *Peptide Science*, 2004, Shimohigashi (Ed.), Japanese Peptide Society, pp. 165-168.

Li et al., "Nonproteinogenic alpha-Amino Acid Preparation Using Equilibrium Shifted Transamination," *Organic Process Research & Development*, 2002, 6:533-538.

Nakamura et al., "Total Synthesis of Monatin," *Organic Letters*, 2000, 2(19):2967-2970.

Nakamura et al., "Total Synthesis of Monatin and the Taste Experience," *Peptide Science*, 2003, pp. 61-64.

Oliveira et al., "Highly diastereoselective alkylation of a pyroglutamate derivative with an electrophile obtained from indole. Synthesis of a potential intermediate for the preparation of the natural sweetener (−)-monatin," *Synthetic Communications*, 2000, 30(12):2143-2159.

Oliveira et al., "Diastereoselective formation of a quaternary center in a pyroglutamate derivative. Formal synthesis of Monatin," *Tetrahedron Letters*, 2001,42:6793-6796.

Tamura et al., "Highly stereoselective synthesis of (−)-monatin, a high-intensity sweetener, using chelation-controlled nitrone cycloaddition," *Chemical Communications*, 2003, 21:2678-2679.

Tamura et al., "Stereoselective Synthesis of 4-Hydroxy 4-Substituted Glutamic Acids," *J. Org. Chem.*, 2005, 70(12):4569-77.

Vleggaar et al., "Structure elucidation of monatin, a high-intensity sweetener isolated from the plant *Schlerochiton ilicifolius*," *J. Chem. Soc. Perkin Transactions 1: Organic and Bio-Organic Chemistry (1972-1999)*, 1992, 22:3095-3098.

Buldain et al., "Carbon-13 Nuclear Magnetic Resnoance Spectra of the Hydrate, Keto, and Enol Forms of Oxalacetic Acid," *Magnetic Resonance Chemistry*, 1985, 23(6):478-481.

Guo et al., "Protein tolerance to random amino acid charge," *Proc. Natl. Acad. Sci. USA*, 2004, 101(25):9205-9210.

Seffernick et al., "Melamine deaminase and atrazine chlorohydrolase: 98 percent identical but functionally different," *J. Bacteriology*, 2001, 183(8):2405-2410.

Seo Jeong-Sun et al., "The genome sequence of the ethanologenic bacterium *Zymomonas mobilis* ZM4," *Nature Biotechnology*, 2005, 23(1):63-68.

Whisstock et al., "Prediction of protein function from protein sequence," *Q. Rev. Biophysis*, 2003, 36(3):307-340.

Witkowski et al., "Conversion of b-ketoacyl synthase to a malonyl decarboxylase by replacement of the active-site cysteine with glutamine," *Biochemistry*, 1999, 38:11643-11650.

Chica at al., "Semi-rational approaches to engineering enzyme activity: combining the benefits of directed evolution and rational design", Current Opinion in Biotechnology, 20, 16, 378-384, 2005.

Fuganti et al., "Kinetic resolution of substituted, 1, 2-4H-5, 6-Dihydrooxazines with carboxylesterase NP", Bioorganic and Medicinal Chemistry, 1994, vol. 2, No. 7, 723-726.

Gosset et al., "A direct comparison of approaches for increasing carbon flow to aromatic biosynthesis in *Escherichia coli*," Journal of Industrial Microbiology, 1996, 17:47-52.

Moriya et al., "A facile synthesis of 6-chloro-D-tryptophan", Bulletin of the Chemical Society of Japan, 1975, 48:2217-2218.

Wolf et al., "A Biocatalytic Route to Enantiomerically Pure Unsaturated -H—Amino Acids," Adv. Synth. & Catalysis, 2001, 343:662-674.

"Cross-Linked Crystals of Subtilisin Versatile Catalysts for Organic Synthesis", Yi-Fong Wang, et al., Annals New York Academy of Sciences, 777-783, 1996.

* cited by examiner

BFD of EBMA Preparation

BFD of ECHA Preparation

ID Reduction and SS/RR Monatin Purification

PRODUCTION OF MONATIN ENANTIOMERS

FIELD

The present invention relates generally to methods for the production of glutamic acid derivatives, their salts and internal condensation products thereof, including methods applicable to the large-scale production of such compounds. More specifically, the present invention relates to methods for the production of 3 (1-amino-1,3-dicarboxy-3-hydroxy-but-4-yl)indole (also known as "monatin"), its salts and internal condensation products thereof, including methods applicable to the large-scale production of monatin.

BACKGROUND

Monatin is a high-intensity sweetener having the chemical formula:

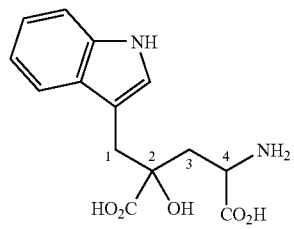

Monatin includes two chiral centers leading to four potential stereoisomeric configurations. The R,R configuration (the "R,R stereoisomer" or "R,R monatin"); the S,S configuration (the "S,S stereoisomer" or "S,S monatin"); the R,S configuration (the "R,S stereoisomer" or "R,S monatin"); and the S,R configuration (the "S,R stereoisomer" or "S,R monatin"). As used herein, unless stated otherwise, the term "monatin" is used to refer to compositions including all four stereoisomers of monatin, compositions including any combination of monatin stereoisomers, (e.g., a composition including only the R,R and S,S, stereoisomers of monatin), as well as a single isomeric form.

For purposes of this disclosure, the monatin carbon backbone will be numbered as illustrated above, with the carbon directly covalently attached to the alcohol group being identified as the 2-position carbon and the carbon directly covalently attached to the amino group being identified as the 4-position carbon. Consequently, references herein to R,R monatin, S,S monatin, R,S monatin, and S,R monatin mean: 2R,4R monatin, 2S,4S monatin, 2R,4S monatin, and 2S,4R monatin, respectively, unless otherwise indicated.

It should be noted that in the literature, the monatin carbon backbone has also been numbered using an alternative convention, with the carbon attached to the alcohol group being the 4-position carbon, and the carbon attached to the amino group being the 2-position carbon. Accordingly, for example, references to 2S,4R monatin in this disclosure would be the same as references to 2R,4S monatin in literature using the alternative numbering convention.

Furthermore, because of various naming conventions, monatin is known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and, 3-(1-amino-1,3-dicarboxy-3-hydroxy-but-4-yl)indole.

Certain isomeric forms of monatin can be found in the bark of roots of the *Schlerochiton ilicifolius* plant located predominately in the Limpopo region, but also in Mpumalanga and the North West Province of South Africa. However, the concentration of monatin present in the dried bark, expressed as the indole in its acid form, has been found to be about 0.007% by mass. See U.S. Pat. No. 4,975,298. U.S. Pat. No. 5,128,482 ("the '482 patent"), which is hereby fully incorporated by reference, proposes a synthetic pathway for preparing monatin and discloses methods for producing monatin and certain intermediates along the pathway.

At least in part because of its sweetening characteristic, it is desirable to have an economic source of monatin. Thus, there is a continuing need to develop methods for the production of monatin.

SUMMARY

The present invention provides novel methods for making glutamic acid derivatives, including monatin, and intermediates used or generated in the methods, including intermediates in a pathway similar to one disclosed in U.S. Pat. No. 5,128,482. One or more of the novel methods of the instant invention may permit, inter alia, more cost-effective production solutions, including opportunities for large-scale manufacture of monatin, and/or increased compatibility with food-grade production of monatin.

In some embodiments, monatin is generated by (1) producing ethyl 2-bromomethylacrylate ("EBMA") from ethyl acrylate via the intermediate ethyl 2-hydroxymethylacrylate ("EHMA"); (2) reacting EBMA with indole magnesium bromide (which can be generated, for example, from the reaction of ethyl magnesium bromide with indole) to form ethyl 2-indolylmethylacrylate ("EIMA"); (3) reacting the EIMA with ethyl chlorohydroxyiminoacetate ("ECHA") (generated, for example, from glycine ethyl ester hydrochloride) to form isoxazoline diethylester ("ID"); and, (4) subjecting ID to a hydrolysis and a hydrogenolysis reaction to generate monatin. As the structure of monatin is that of a glutamic acid derivative, methods for the synthesis of monatin disclosed herein may also be useful for synthesizing glutamic acid derivatives.

DESCRIPTION

Unless otherwise specified, the terms "include," "includes," "including" and the like are intended to be open-ended. Thus, for example, "include" means "include but are not limited to."

Except as otherwise noted, the articles "a," "an," and "the" mean "one or more."

As used herein, the term "about" encompasses the range of experimental error that occurs in any measurement. Unless otherwise stated, all measurements are presumed to have the word "about" in front of them even if the word "about" is not expressly used.

The term "alkyl" as employed herein by itself or as part of another group refers to both straight and branched chain saturated radicals of up to 10 carbons, unless the chain length is otherwise limited, such as methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, decyl and the like.

As used herein, the term "indole substrate" includes an indole molecule unsubstituted or substituted at one or more of positions 2, 4, 5, 6, and 7 with one or more substituents chosen from alkyl, carboxy, alkoxy, arylalkyl, arylalkoxy, dialkylaminoalkyl, dilakylaminoaryloxy, and dialkylaminoalkoxy.

As used herein, $R^1$ is chosen from hydrogen, alkyl, aryl, or acyl (including arylcarbonyl groups such as benzoyl).

As used herein, $R^2$ and $R^3$ are independently chosen from amides, alkoxy, aryloxy, or aryl substituted alkoxy groups, which are straight chained, branched chain or cyclic, and which optionally contain elements of chirality.

As used herein, Ra-Re are independently chosen from hydrogen, alkyl, carboxy, alkoxy, arylalkyl, arylalkoxy, dialkylaminoalkyl, dilakylaminoaryloxy, and dialkylaminoalkoxy; or any pair of Rb/Rc, Rc/Rd, or Rd/Re may form an alkylene or an alkylenedioxy group.

As used herein, "X", when in a chemical composition formula, is chosen from halides or pseudohalides. A pseudohalide is a leaving group essentially equivalent to halides with respect to leaving group character, such as for example methanesulfonyl or toluenesulfonyl.

As used herein, unless stated otherwise, the term "monatin" is used to refer to compositions including all four stereoisomers, compositions including any combination of monatin stereoisomers (e.g. a composition including only the R,R and S,S stereoisomers of monatin), as well as a single isomeric form.

Figure 1:
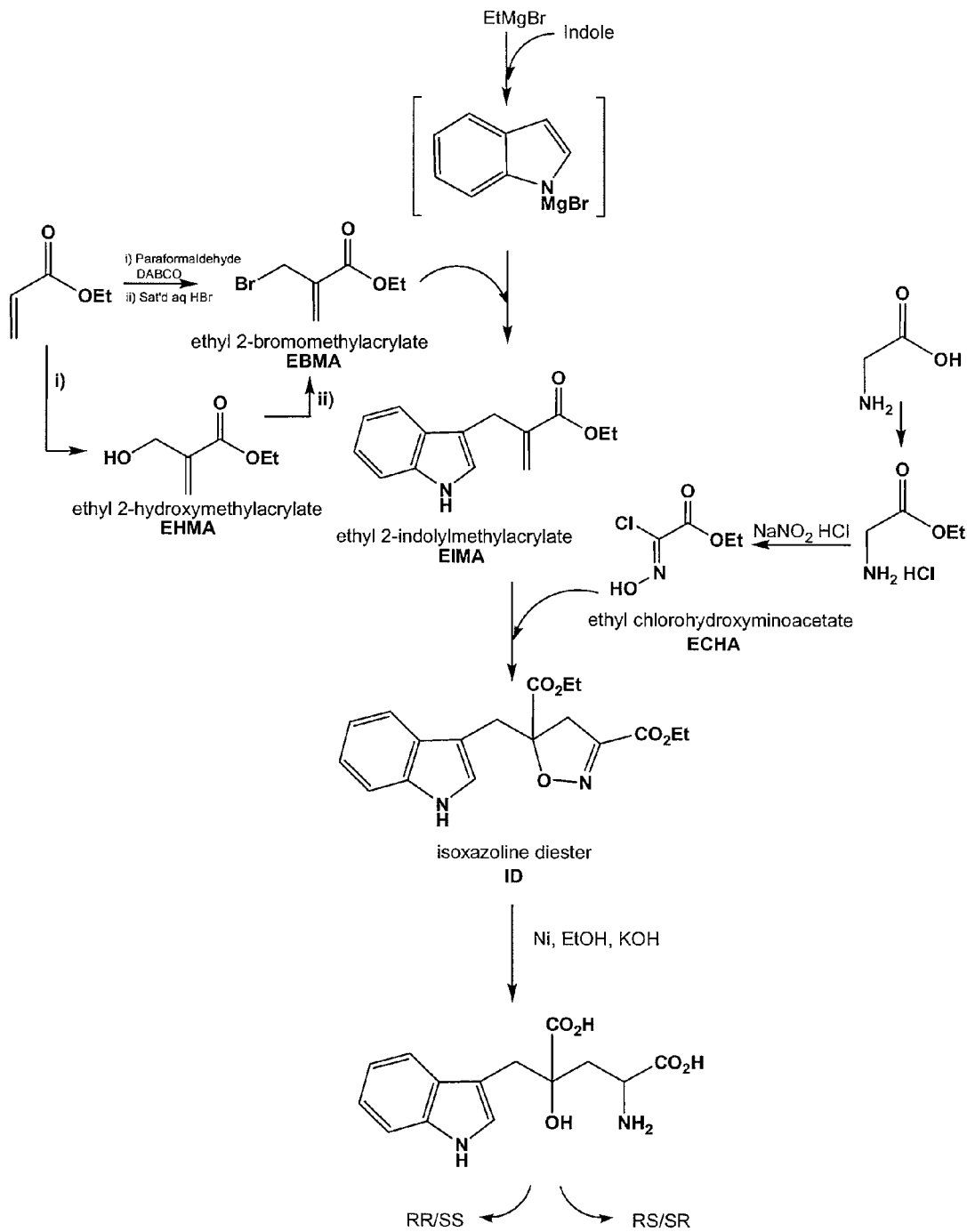
FIG. 1 illustrates a specific embodiment of a pathway for making monatin, and certain intermediates in the pathway, in accordance with the present invention.

Generally, the class of compounds identified by Formula I:

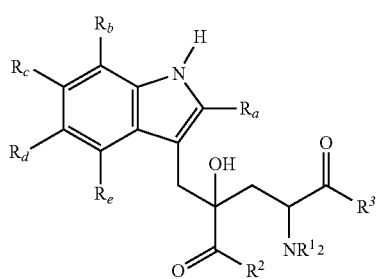

where the two $R^1$ groups on the nitrogen atom can be the same or different,
can be produced by a general process similar to that shown in FIG. 1. The identified reactions may be performed stepwise, or combinations may be performed in a single procedure, and include one or more of the following: reacting an acrylic acid derivative of formula (II)

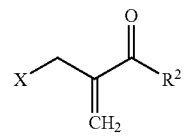

with an indole or an indole derivative of formula III,

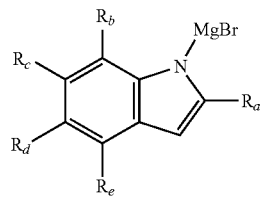

generating a compound of formula (IV);

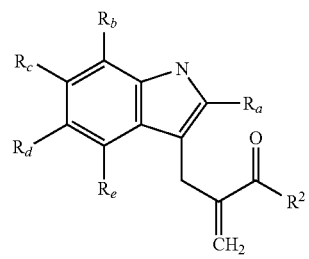

reacting the compound of formula (IV) with a hydroxyimino carboxylate according to formula (V),

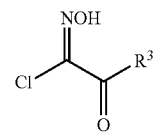

to generate an isoxazoline diester of formula (VI),

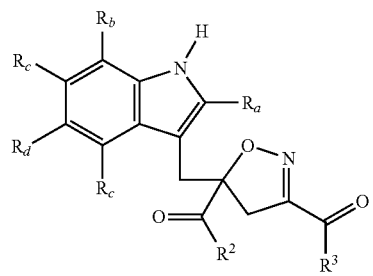

wherein the hydroxyimino carboylate according to formula (V) generates a glycine derived nitrile oxide in situ as the reactive species;
submitting the isoxazoline diester of formula (VI) to conditions under which it will undergo hydrolysis and hydrogenolysis in one reaction vessel to generate compounds of formula (Ia);

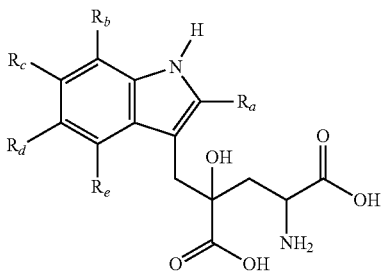

(Ia)

or, alternatively, hydrolyzing the compound of formula (VI) to a compound of formula (VIa)

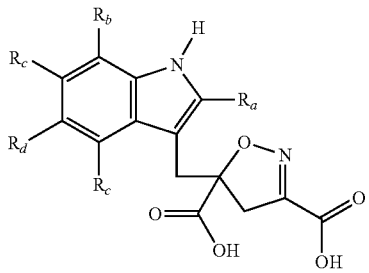

(VIa)

followed by hydrogenolysis to afford a compound of formula (Ia).

An example of an indole derivative with which the acrylic acid derivative of formula (III) can be reacted is the magnesium bromide salt of a deprotonated indole.

The isoxazoline diester of formula (VI) may be racemic, scalemic or enantiomerically pure, depending upon the protocol used upstream.

The methods of production of glutamic acid derivates according to the present invention may also include producing compounds of formula II from acrylate compounds of formula (VII):

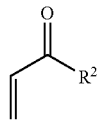

VII via the intermediate of formula (VIII):

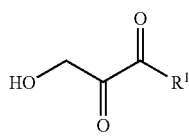

VIII

The methods of production of glutamic acid derivatives according to the present invention may also include producing the compounds of formula V by a nitrosation of glycine esters of formula (IX) (which in turn can be produced by esterification of glycine):

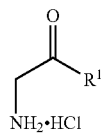

IX

In some embodiments, the glutamic acid derivative is monatin, and the methods of production of glutamic acids can be used to, or adapted to, generate salts, specific isomers, and internal condensation products of monatin. FIG. 1 shows an overall scheme for producing monatin in accordance with an embodiment of the invention. FIGS. 2-7 provide further details of specific embodiments for the various reactions comprising the overall scheme.

Thus, as shown in FIG. 1 monatin can be generated by (1) producing ethyl 2-bromomethyl acrylate ("EBMA") from ethyl acrylate via the intermediate ethyl 2-hydroxymethylacrylate ("EHMA"); (2) reacting EBMA with indole magnesium bromide (which can be generated, for example, from the reaction of ethyl magnesium bromide with indole) to form ethyl 2 indolylmethylacrylate ("EIMA"); (3) reacting the EIMA with ethyl chlorohydroxyiminoacetate ("ECHA") (generated, for example, from glycine ethyl ester hydrochloride) to form isoxazoline diethylester ("ID"); and, (4) subjecting ID to a hydrolysis and a hydrogenolysis reaction to generate the four diastereomers of monatin. As shown, the process may further include separating one set of enantiomeric pairs from the other set, i.e., separating the RR/SS enantiomeric pair from the RS/SR enantiomeric pair.

Figure 2:
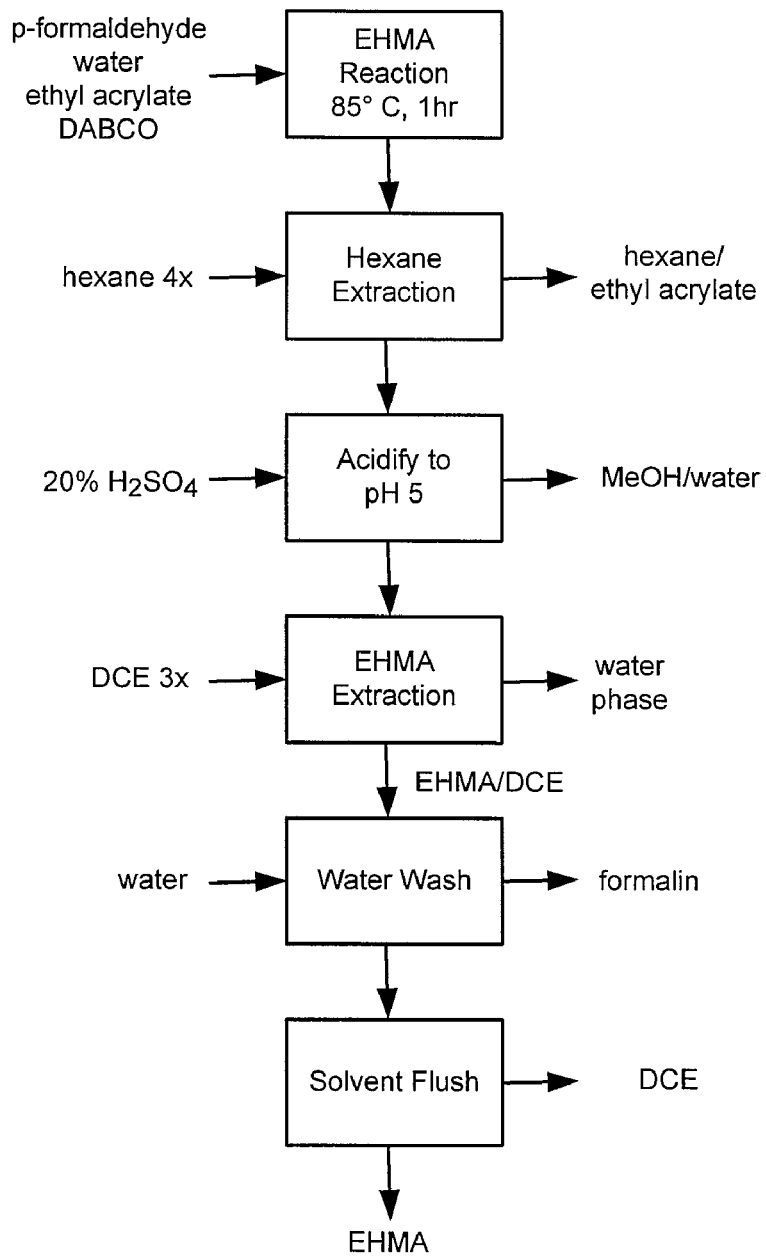
FIG. 2 is a flow diagram of a specific embodiment for the production of EHMA in accordance with the present invention.

FIG. 2, together with Example 1, provide details of an approach for preparing EHMA. Specifically, EHMA is produced from ethyl acrylate in a biphasic reaction mixture. The inventors found that using a biphasic, rather than neat—or solventless system as taught in the '482 patent—can result in fewer by-products. This discovery enabled isolation of the target product by extraction, which isolation method can provide for better selection than a distillation process and consequently can improve yield and purity of downstream products, and can provide the benefit of being compatible with large-scale synthesis.

Figure 3:
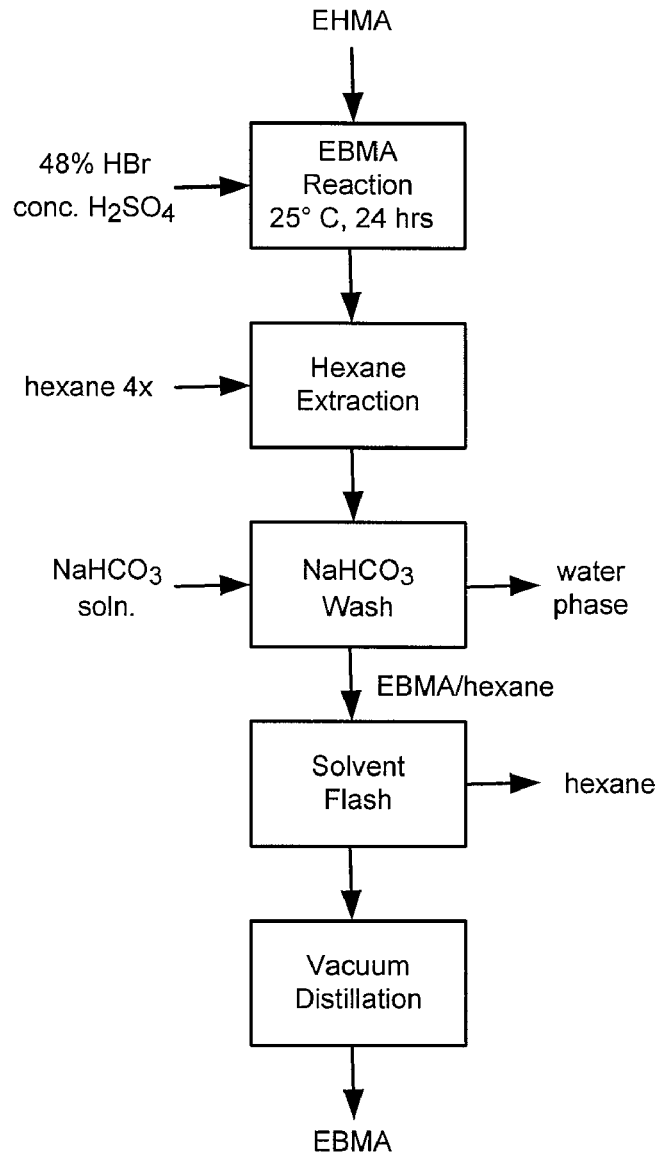
FIG. 3 is a flow diagram of a specific embodiment for the production of EBMA in accordance with the present invention.
Figure 4:
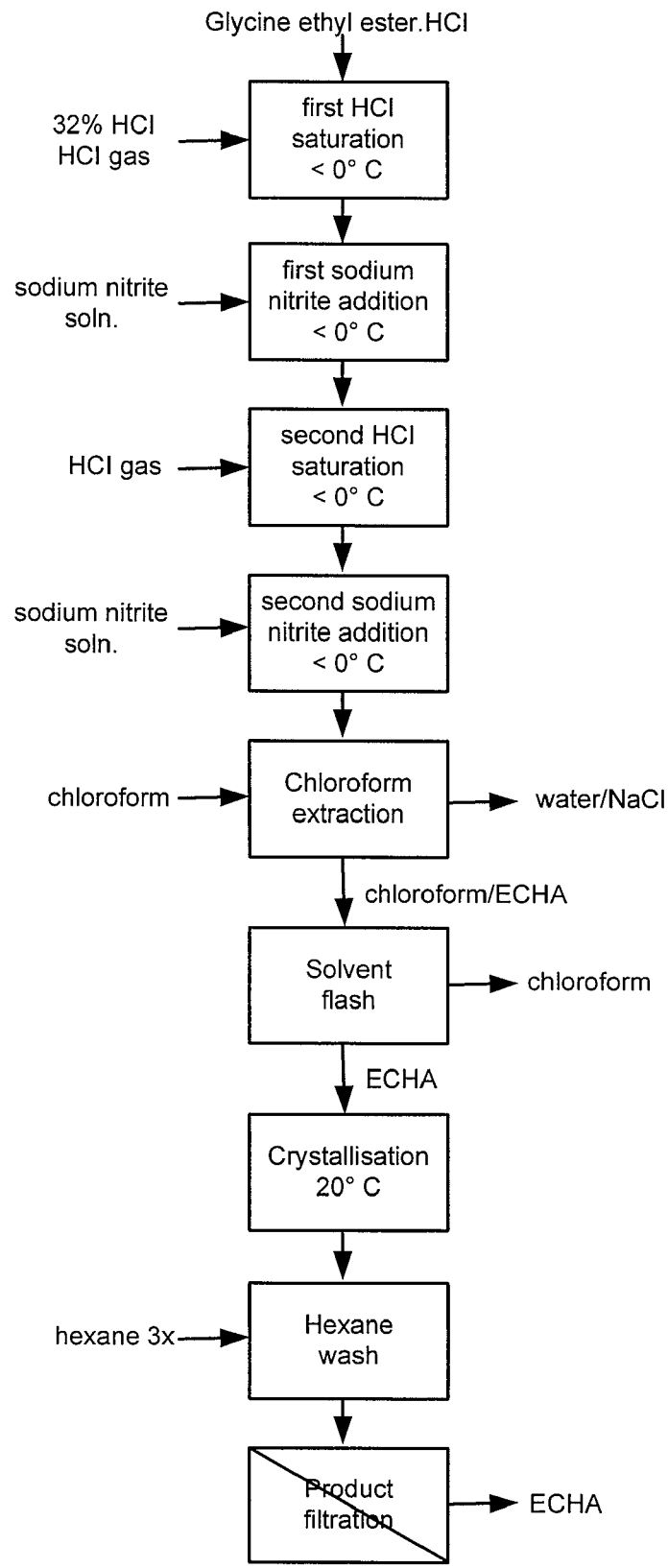
FIG. 4 is a flow diagram of a specific embodiment for the production of ECHA in accordance with the present invention.

FIG. 3 provides details of an approach for preparing EBMA. Specifically, EBMA is produced from the reaction of EHMA with a concentrated aqueous HBr solution. The inventors found that using concentrated sulphuric acid can result in faster and more selective reactions resulting in fewer by-products and easier isolation of the product. The EBMA is recovered from the reaction mixture by extraction with hexane. The hexane layer is washed several times with a sodium bicarbonate solution to remove acidic residues. Hexane is then removed by evaporation to yield a crude EBMA product. This crude mixture is distilled under vacuum to yield pure EBMA FIG. 4 provides details of an approach for preparing ECHA. Specifically, ECHA is prepared by the reaction of glycine ethyl ester hydrochloride with nitrosyl chloride gas. Nitrosyl chloride gas is generated in situ by the reaction of sodium nitrite with concentrated aqueous hydrochloric acid. The reaction is highly exothermic and carried out at temperatures below 0° C. Hydrogen chloride gas is first sparged through the reaction mixture to generate the concentrated hydrochloric acid solution. A solution of sodium nitrite is then slowly dosed into the reaction mixture to generate nitrosyl chloride gas. These steps are repeated and results in improved yields of ECHA. The reaction mixture is then extracted with chloroform and the solvent is flash distilled to leave an oily residue. This oily residue crystallises upon cooling to ambient temperature. The crystals are washed with cold hexane to remove by-products, and dried in vacuo to produce a pure, white product. The inventors found that improved purities and recoveries of ECHA could be obtained if the product is extracted into chloroform. In previous experiments ECHA was crystallised directly from the aqueous reaction mixture. This procedure resulted in poor recoveries, was not scalable or reproducible and the product isolated was contaminated with sodium chloride.

Figure 5:
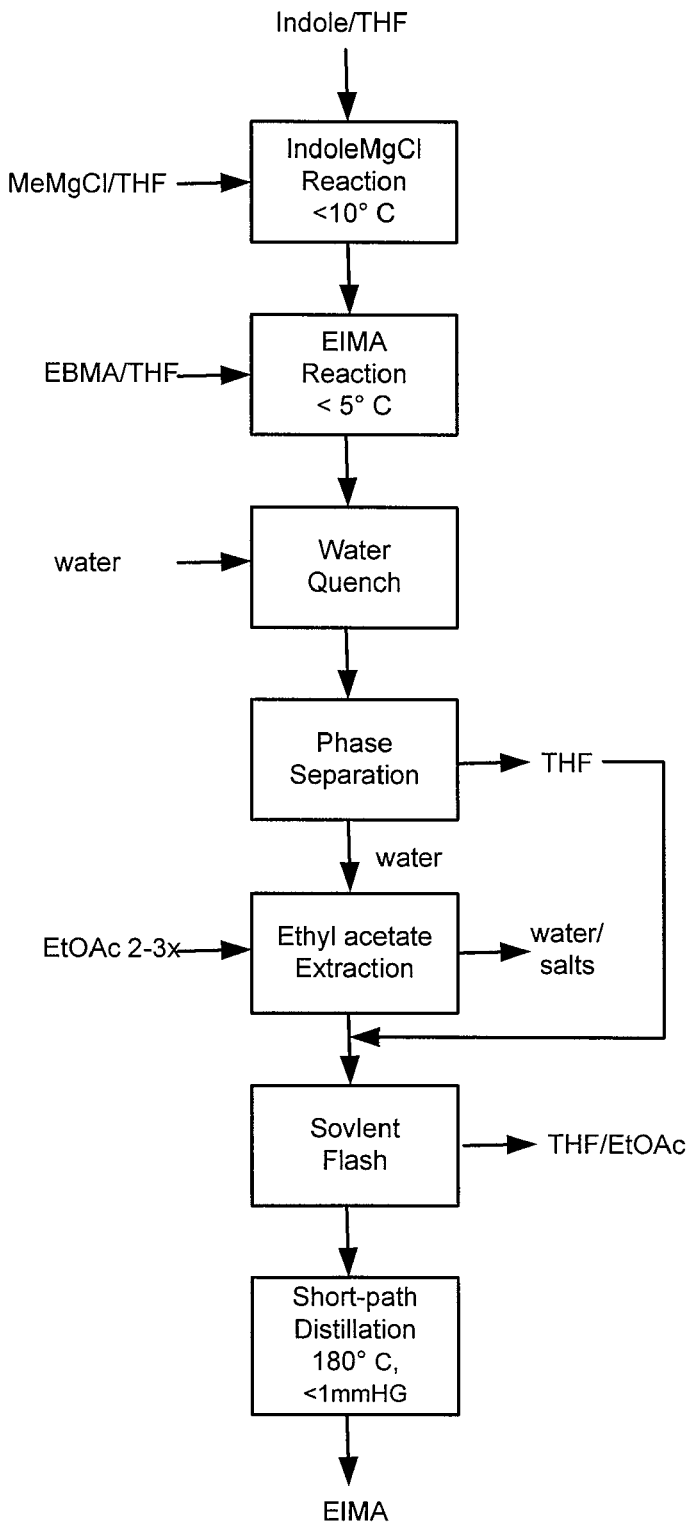
FIG. 5 is a flow diagram of a specific embodiment for the production of EIMA in accordance with the present invention.

FIG. 5 together with Example 9, provides details of an approach for preparing EIMA. Specifically, EIMA is produced from the addition of methylmagnesium chloride to a solution of indole in tetrahydrofuran (THF) to generate indolemagnesium chloride. While ensuring that the temperature did not exceed 30° C., the reaction was typically carried out between 6-10° C. A solution of EBMA in THF was then added over the required time while ensuring that the reaction temperature did not exceed 5° C. During the EBMA/THF addition, the reaction is highly exothermic and reaction temperature is controlled by varying the dosing rate. The reaction is then quenched using water, followed by phase separation. Alternatively, the reaction may be quenched with a saturated aqueous ammonium chloride solution, followed by washing with a saturated aqueous sodium chloride solution. Due to the miscibility of THF in water the aqueous phase is then extracted (2×) with ethyl acetate. The combined organic phases are concentrated under reduced pressure. The crude organic residue is then transferred hot into the feed vessel of the short path distillation (SPD) unit. Passing the material through the SPD facilitates the separation of the EIMA product from the high boiling by-products, thus limiting thermal decomposition. A typical yield between 45-54% and product purity between 70-75% by % m/m was achieved.

Figure 6:
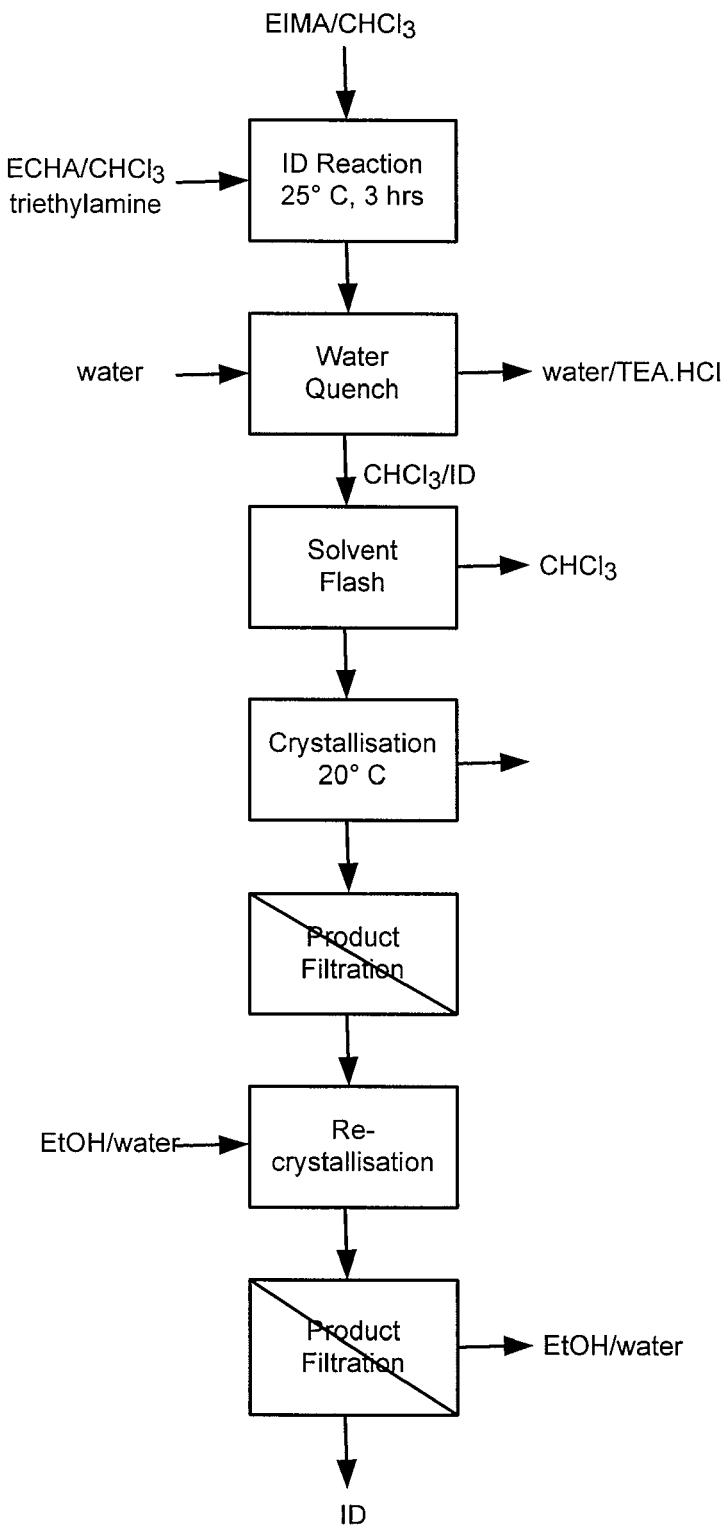
FIG. 6 is a flow diagram of a specific embodiment for the production of Isoxazoline diester in accordance with the present invention.

FIG. 6 provides details of an approach for preparing ID. Specifically, Specifically, isoxazoline diester is formed by the reaction of EIMA with ECHA in a solvent such as chloroform in the presence of an amine base such as triethylamine. The reaction can be carried out up to 6 times more concentrated than taught in the '482 patent, significantly reducing batch volumes. The reaction is complete within 2-4 hours on large scale, and it is not necessary to leave the reaction for longer periods of time (up to 24 hours) as described in the '482 patent. Higher concentrations and shorter reaction times make for more efficient production on large scale. The reaction is quenched with water, and the organic phase separated. Removal of solvent affords the crude ID, which is purified by recrystallisation from water/ethanol to afford pure ID. EIMA of purity >70% functions well in this reaction.

Figure 7:
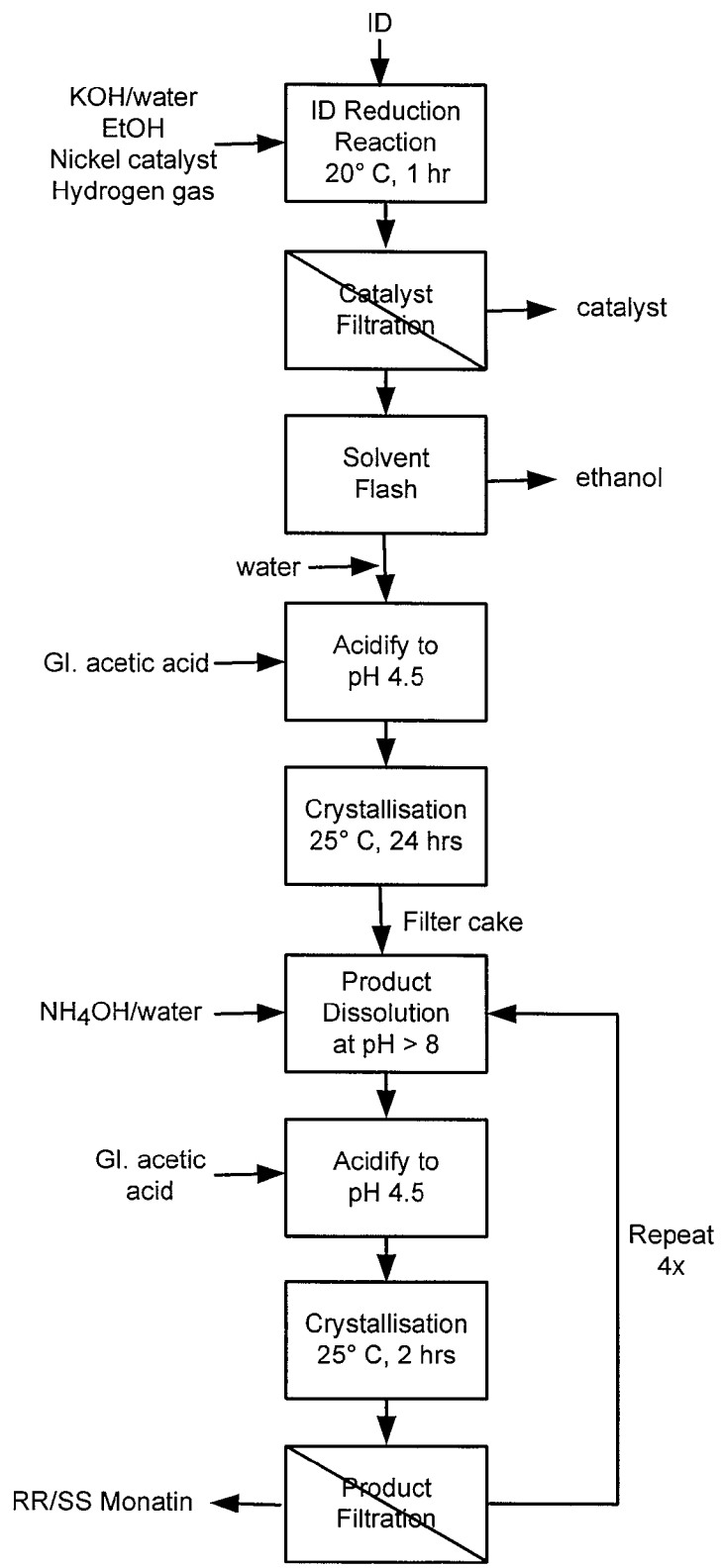
FIG. 7 is a flow diagram of a specific embodiment for the preparation and purification of monatin in accordance with the present invention.

FIG. 7 provides details of an approach for preparing and purifying Monatin. Specifically, where the ID is submitted to hydrogenolysis, the matrix used for hydrogenolysis is sufficient to initiate chemical hydrolysis due to the basicity of the system. Most preferably, this hydrogenolysis is carried out in an alcohol/water system at a temperature slightly above room temperature. The monatin so generated may be racemic, or if a chiral ester group or enzymatic hydrolysis has been employed upstream, enantiomerically enriched.

The diastereomers generated may be separated by fractional crystallization. The RR/SS diastereomer or enantiomerically enriched variants thereof may be precipitated from a largely aqueous stream. The RS/SR diastereomer or enantiomerically enriched variants thereof may be precipitated from an ethanol rich stream.

Where the diastereomers have been isolated in diastereomerically pure form, the enantiomeric purity can be enriched by the generation of salts with a chiral amine. Cinchona alkaloids, alkyl glucamines and phenethyl amine derivatives may be useful in this respect.

If one diastereomer is required, the diastereomers can be interconverted by means of generating an amide on the nitrogen terminus, followed by treatment with a base. An embodiment of the amide generation step is the generation of a benzamide derivative of formula I wherein one of $R^1$ is H and the other is benzoyl; however, other acyl groups may also be used.

Generally, the amide functionality of the compound of formula (I) in which one of the $R^1$ groups is benzoyl can be removed by chemical hydrolysis, generating a compound of formula (Ia)

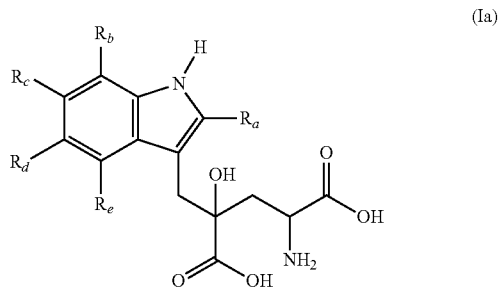

(Ia)

from which the individual diastereomers can be isolated by crystallization as described above. This cycle of acylation, epimerization and hydrolysis can be repeated several times—over time generating a single diastereomer.

As shown, chemical hydrolysis of VIa may be accomplished in a water based matrix, using, for example, sodium hydroxide, potassium hydroxide or ammonia solution. A water miscible organic solvent such as (but not limited to) ethanol, methanol, or dioxane can be used as a co-solvent to promote diester solubility in this step.

Some embodiments for producing compounds of formula (II) involve producing an alkyl or aryl 2-chloromethylacrylate as the acrylic acid derivative via the alkyl or aryl 2-(hydroxymethyl)acrylate intermediate. Some embodiments involve producing ethyl 2-chloromethylacrylate ("ECMA") via the ethyl 2-(hydroxymethyl)acrylate intermediate, as an alternative to producing EBMA. Examples 2 and 3 provide sample protocols for producing ECMA from EHMA.

By surprisingly finding—contrary to the expectations of those of ordinary skill in the art—that chloride could not only be substituted for bromide in the process disclosed in the '482 patent, but also provided comparable, if not better, results, the inventors solved a need for a more efficient, cost-effective process. Persons of ordinary skill generally understand that if a reaction is to proceed at all when chloride is substituted for bromide, significant process changes are required, and in any case the reaction would likely proceed more sluggishly. Consistent with this expectation, the inventors found that when thionyl chloride was used the reaction did not produce the required product. Yet, surprisingly, the reaction proceeded quite well when hydrogen chloride was used.

More specifically, the process of the '482 patent uses EBMA as the addition product to the Grignard reagent. While good yields are obtained with the Baylis-Hillman reaction to produce EHMA, the bromination of EHMA requires highly concentrated HBr solutions for an efficient reaction. The highest concentration of HBr commercially available is only 48% and the reaction is very inefficient using this alone. This means that HBr has to be generated (from tetralin and bromine) or an HBr gas cylinder has to be used to sparge HBr gas through the reaction mixture. While good yields are obtained with these processes, it is not economically feasible on a larger scale. As demonstrated by the inventors, sulfuric acid can be used as a dehydrating agent to concentrate HBr, but the yields from these particular reactions were very low. The overall yield over the EHMA and bromination process was only about 30%.

In order to offset the costs inherent in the preparation of EBMA and the inefficiencies detailed above, the preparation of the potentially cheaper chloro derivative ("ECMA") was examined. The purity of the ECMA was about 92% with minimal formation of by-products. Reactions carried out in 32% HCl with the addition of HCl gas proved effective. The addition of HCl gas under cold conditions and the sealing of the reactor ensured that the reaction was carried out in an HCl-rich environment resulting in efficient reaction. Reaction with thionyl chloride did not produce the required product.

Some embodiments for production of formula (II) compounds involve producing an alkyl 2-bromomethylacrylate in reaction mixture including an alkyl 2-hydroxymethylacrylate and an aqueous hydrogen bromide solution and sulfuric acid, and/or purifying the so-produced alkyl 2-bromomethylacrylate prior to its use in generating alkyl 2-indolylmethylacrylate. Example 4 provides a protocol for producing alkyl 2-bromomethylacrylate in an embodiment according to the invention.

Some embodiments for production of formula (II) compounds involve producing an ethyl 2-bromomethylacrylate ("EBMA") in a reaction mixture including EHMA and an aqueous hydrogen bromide solution and sulfuric acid and purifying the so-produced EBMA from the reaction mixture prior to its use in generating ethyl 2-indolylmethylacrylate ("EIMA"). Example 5 provides a protocol in accordance with an embodiment of the invention for producing EBMA.

The '482 patent discloses a process for producing EBMA, which is carried out in neat ethyl acrylate and utilizes hydrobromic gas. In contrast to the inventive process, the reaction process of the '482 was not selective (<50%) to EBMA, produced numerous by-products visible on the GC traces, and produced product with a purity of ~80% at small scale, which purity was barely reproducible, difficult to achieve, and resulted in considerable loss of material at large scale. Embodiments of the inventive process for producing EBMA can provide a purity of >95% at a reasonable yield.

Some embodiments for producing formula (IV) compounds involve producing alkyl 2-indolylmethylacrylate by reacting an alkyl 2-chloromethylacrylate, with an indole magnesium halide. One embodiment involves producing ethyl 2-indolylmethylacrylate ("EIMA") by reacting ECMA with an indole magnesium bromide. Example 6 provides a protocol for producing EIMA from ECMA in accordance with an embodiment of the invention. Whereas those of ordinary skill would have expected that chloride may not function in the reaction, or would require significant process changes such as higher temperatures yet still result in a slower reaction, here again, the inventors surprisingly developed a chloride reaction, without significant process changes, and with comparable reaction efficiency to bromide. (See e.g. A R Katritzy, O Meth-Cohn, C W Rees Eds; 1955, Volume 1, pg. 107: "iodide and bromide are the best leaving groups, alkyl chlorides react at much slower rates.")

According to an embodiment of the present invention, the alkyl 2-indolylmethylacrylate, from the reaction of an alkyl 2-halomethylacrylate with an indole magnesium halide, is purified using a distillation process prior to its use as a reagent in the reaction to form ID and/or the alkyl 2-indolylmethylacrylate purified by distillation is used to form isoxazoline diester. "Purified" means only that the target compound contains fewer impurities than as found in the reaction mixture; however, the target compound may still contain significant impurities. For example, an alkyl 2-indolylmethylacrylate which is isolated from the reaction mixture using distillation to a 70% purity level would be considered "purified." Example 7 generically describes a process for preparing EIMA, presents comparisons of purification procedures and impact on ID yield. Examples 8 through 10 illustrate protocols for producing EIMA from EBMA.

The inventors surprisingly discovered that a distillation process could be compatible with the desired purification, contrary to what is understood by those of ordinary skill in the art, that distillation is an unlikely method of purification for non-volatile viscous oils. In fact, consistent with the expectations of the art, the classical distillation process resulted in significant decomposition at the 2 L scale. The inventors, however, surprisingly discovered that a wiped-film short path distillation could successfully separate the product from the high-boiling by-product. A benefit of purification by distillation versus chromatography is that the former process is scalable—i.e. adaptable to large-scale production—whereas the latter process is not. Further, persons of ordinary skill generally expect that high purity is desirable for achieving suitable yields. Consistent with this expectation, for example, the purity of EBMA starting material has a significant effect on the performance of the Grignard reaction. When EBMA of purity <90% was used, a significant decrease in conversion of indole was noted. This resulted in additional molar equivalents of Grignard reagent required for reaction, and an overall decrease in yield of product of approximately 10%. The inventors, however, surprisingly discovered that EIMA of greater than 50% purity, and preferably greater than 70% purity could be used to produce yields of isoxazoline diethyl ester ("ID") at large scale that are comparable to the small scale chromatography yields.

Some embodiments of the present invention involve facilitating the production of ethyl chlorohydroxyiminoacetate ("ECHA") by saturating the reaction mixture with gaseous HCl and/or isolating ethyl chlorohydroxyiminoacetate using an extraction rather than a crystallization process. Example 11 describes a protocol for preparing ethyl chlorohydroxyiminoacetate ("ECHA") and compares yields from the inventive process to the prior art. Example 12 provides an example of large-scale production of ECHA in accordance with the invention. Example 13 provides another example of ECHA production in accordance with the invention. These new methods of producing ECHA resulted in higher yields (averaging approximately 56.7%) at 140 and 210 g scales as compared to the '482 patent (which produced a yield of approximately 25% at 70 g scale and less than 20% at about 140 g scale), and a scaleable process.

According to some embodiments of the invention, the diester of Formula VI is isoxazoline diester ("ID"), and the ID is produced from EIMA. Example 14 illustrates a protocol in accordance with the invention for producing ID from EIMA.

Some embodiments for production and hydrogenolysis of formula (VI) compounds involve producing monatin from the ID in a one-step process—rather than multi-step process—, which accomplishes both hydrolysis and reduction of the isoxazoline diester. According to some embodiments of the present invention, a Rhodium catalyst, and preferably a sponge nickel catalyst facilitate the one-step hydrolysis/hydrogenation reaction. According to some embodiments, the one-step hydrolysis/hydrogenation utilizes a catalyst chosen from Sodium amalgam, Rhodium on charcoal, Palladium on charcoal, Platinum on charcoal, Palladium on alumina, Ruthenium on charcoal, Raney nickel, and Sponge Nickel Catalysts (For example, a series of Sponge Nickel catalysts from AMC, i.e. A7063, A7000, A5200, A5000, A4000), and supported nickel catalysts such as Kata Levina 6564. According to some embodiments the catalyst as chosen from 5% Sodium amalgam, nickel A7063, nickel A7000 dispersed in water, Nickel A7000 dispersed in oil, Nickel A5200, Nickel A5000 dispersed in water, Nickel A4000, and 5% Rhodium on charcoal. Example 14 illustrates an embodiment for the preparation of ID. Examples 15-23 illustrate the reduction of ID to form monatin using metal catalysts. Examples 15 and 22 further illustrate a method for the separation of the four diastereomers to two pairs of enantiomers.

The successful application of sponge nickel and rhodium catalysts to the reduction of ID to form monatin, and further under the conditions set forth, was an unexpected and surprising outcome that was contrary to the teachings of the art. The reduction of the isoxazoline diester (or diacid) comprises a complex series of events, the sequence and relative rates of which impact the successful generation of the required product. If the diester is considered, the events in question can be termed ester hydrolysis (two hydrolytic events), nitrogen-oxygen bond reduction and reduction of the pseudoimine (carbon-nitrogen double bond). Successful transformation is related to reducing the carbon-nitrogen double bond before the nitrogen-oxygen bond, all of which must be carried out in the presence of the sensitive indole nucleus. Should this condition fail to be satisfied (the nitrogen-oxygen bond reduction preceding the reduction of the carbon-nitrogen double bond) the aliphatic imine so formed would be subject to a highly facile hydrolysis, generating a pyruvate α-ketoacid) derivative. Under reducing conditions, pyruvate derivatives of this type generate α-hydroxyacid derivatives that could not be readily converted to the required amino acid derivative.

In such situations, reduction techniques involving single electron transfer are typically used to ensure that the carbon-nitrogen double bond is reduced first. Of these techniques, dissolving metal reductions figure prominently. Mechanistically, such techniques are initiated through the transfer of a single electron to a π-system, the rate of which is enhanced where the system receiving the electron contains a heteroatom (such as oxygen or nitrogen). In this type of reduction there is very little ambiguity as to the sequence of events—suggesting that use of a single electron transfer agent such as sodium metal (typically as an amalgam) would be the reduction protocol of choice (see U.S. Pat. No. 5,128,482). Generation of the hydroxy compound can also be problematic in dissolving metal reductions, particularly where samarium iodide is used (Sun Ho Jung, Jee Eun Lee and Hun Yeong Koh, *Bull. Korean Chem. Soc.,* 19, 33 (1998)). Further, the dissolving metal reduction using a sodium/mercury amalgam requires the use of a large excess of sodium amalgan (7 molar equivalents of sodium as a 5% amalgam). This in turn, requires large quantities of mercury, which is expensive and toxic, for the bulk preparation of sodium amalgam, and the process is not safe for large scales. In addition, the use of mercury in the preparation of a food grade product is not considered appropriate. Consequently, this approach was not appropriate for reducing ID.

Catalytic metal/hydrogen systems, however, show no such clear-cut mechanistic bias for the required reactivity. Both Nickel (K. B. G. Torssell, O. Zeuthen, *Acta Chem. Scand. Ser. B,* 32, 118 (1978); R. H. Wollenberg, J. E. Goldstein, *Synthesis,* 1980, 757; A. P. Kozikowski, M. Adamczyk, *Tetrahedron Lett.,* 23, 3123 (1982); S. F. Martin, B. Dupre, *Tetrahedron Lett.,* 24, 1337 (1983); D. P. Curran, *J. Am. Chem. Soc.,* 104, 4024 (1982); D. P. Curran, *J. Am. Chem. Soc.,* 105, 5826 (1983)) and palladium catalysts (Sun Ho Jung, Jee Eun Lee, Hyun Jung Sung and Soon Ok Kim, *Bull. Korean Chem. Soc.,* 17, 2 (1996)) have been reported to generate the hydroxy compound in the reductions of isoxazolines under hydrogenolysis conditions—an outcome consistent with the reduction of oximes by nickel catalysts in aqueous alkaline solution (B. Staskun and T. van Els, *J. Chem. Soc.©,* 1966, 531). Under strictly anhydrous conditions, Nickel catalysis has been used to effect hydrogenolysis of simple isoxazoline diesters in the presence of benzoic anhydride (Virgil Helaine and Jean Bolte, *Tetrahedron Asymmetry,* 9, 3855 (1998)). The conditions required for hydrolysis of the resulting amide, however, rendered this approach less attractive for the current application.

The reduction of the isoxazoline diester using catalytic hydrogenolysis was examined where the substrate was in both acid and ester forms. On the basis of the limited precedent identified, anhydrous conditions were employed initially. Conditions similar to those employed by Bolte failed to give a satisfactory outcome. None of the conditions examined under anhydrous conditions (both nickel and palladium species as catalyst) gave satisfactory results. Aqueous conditions (non basic or of limited alkalinity as taught by the prior art of Staskun) also failed to generate the required outcome. Similarly, acidic media failed to give the required result.

Unexpectedly, it was only under strongly alkaline conditions that the required species became the major product of catalytic hydrogenolysis. Palladium or ruthenium catalysis resulted in an incorrect reaction pathway and product, while platinum catalysis failed to effectively promote the reaction with only 5% of the desired product formed. Palladium catalysis, while promoting the incorrect pathway as the major route, did produce the required product. Somewhat more success was observed when nickel catalysis was used, although this was not a general result. Supported nickel catalysts (such as those supplied by Kata Leuna) failed to generate product. Similarly, rhodium catalysis resulted in formation of the required product. Ultimately, it was determined that catalysts loosely described as "sponge nickel" proved particularly suitable to effect the required transformation (most particularly A7063, A4000, A5000, A5200, A7000, preferably in water dispersion form as supplied by Active Metals Corporation) under relatively low hydrogen pressures (of the order of 1-5 bar) at around room temperature in aqueous ethanolic alkali metal hydroxide solution.

While multiple embodiments are disclosed herein, still other embodiments of the present invention will become apparent to those skilled in the art from the following detailed description, which shows and describes illustrative embodiments of the invention. As will be realized from the description herein, the invention is capable of modifications in various aspects, all without departing from the spirit and scope of the present invention. Accordingly, the drawings, and detailed specification including the examples, are to be regarded as illustrative in nature and not restrictive.

Unless otherwise indicated, all numbers expressing quantities of ingredients, reaction conditions, and so forth used in the specification and claims are to be understood as being modified by the term "about." Accordingly, unless indicated to the contrary, such numbers are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

The invention will now be described in more detail with reference to the following non-limiting examples:

EXAMPLE 1

A 2-4 molar excess of paraformaldehyde (or aqueous formalin solution) dissolved in water is mixed with a solution of ethyl acrylate in which is dissolved a basic catalyst (1-20 mol % DABCO or DBU). After acidifying the reaction mixture (at room T) to pH 5, the mixture is extracted with a water immiscible solvent (chloroform, dichloroethane, dichloromethane). The organic layer is washed with water and the organic phase is distilled under vacuum to remove the solvent. The conversion of ethyl acrylate ranges from about 60-80% and the product, EHMA is isolated at a purity of >85%.

EXAMPLE 2

Preparation of ECMA

EHMA (100 g, 0.77 mol) and zinc chloride (102 g) were charged into a round bottom flask equipped with thermometer and condenser. The mixture was heated to reflux (80° C.) for 4 hours. The reaction mixture was then cooled to room temperature and extracted with diethyl ether (3×100 g). The mixture was concentrated under vacuum (40-50° C.) to obtain a product of 85% purity (7.5 g, 6.5% yield).

EXAMPLE 3

Preparation of ECMA

EHMA (5 g, 0.038 mol) was dissolved in conc. HCl (32%) and the solution was cooled to 2° C. using a salt/ice bath. HCl gas was then sparged through the solution for 10 minutes. The reactor was sealed and left to warm up to room temperature overnight. It was observed that the solution had separated into two phases. The mixture was extracted with hexane (3×20 ml). The mixture was concentrated under vacuum (50° C., 10 mm Hg) to obtain a product of 92% purity by GC.

EXAMPLE 4

Preparation of EBMA

EHMA is dissolved in a mixture of 48% aqueous hydrobromic acid and concentrated sulfuric acid and the mixture is stirred at 25° C. for 24 hours. The reaction mixture is then extracted with a water immiscible solvent (petroleum ether, hexane, heptane), the organic phase is washed with a dilute solution of sodium bicarbonate and the crude product is concentrated under vacuum to afford the compound of Formula II at a purity of >95%.

EXAMPLE 5

Pilot Plant Scale Preparation of EBMA

Paraformaldehyde (18.75 kg, 625 moles) was added to water (62.5 kg) in the reactor. To this mixture, DABCO (0.10 eq, 2.8 kg, 25 moles) and ethyl acrylate (25 kg, 250 moles) were added. The contents were heated to 85° C. Reaction progress was monitored by GC analysis of samples collected at different reaction time intervals. After maximum conversion had been reached, the reaction mixture was cooled to 25° C. and treated with aqueous sulfuric acid (4.35 kg of 20% solution) to adjust the pH of the mixture to 4.5. The reaction mixture was extracted with hexane (16.5 kg) which was pumped into the reactor. The contents were then stirred for 30 minutes, after which the stirrer was stopped and the contents were allowed to settle for 30 minutes. The phases were separated and the aqueous phase pumped back to the reactor. This process was repeated twice to facilitate removal of ethyl acrylate and some by-products. The remaining aqueous phase was then extracted with 1,2-dichloroethane (DCE, 20 kg). The contents were stirred for 30 minutes, stirrer stopped and mixture allowed to settle (this usually required 2 hrs). The phases were then separated and the aqueous phase transferred back to the reactor and the extraction process repeated twice. The DCE extract was then analyzed for residual paraformaldehyde. This was done by adding a 2 g sample of the extract to 100 ml of 125 g/l solution of sodium sulfite. Three drops of phenolphthalein were added and the mixture titrated to a colorless end point with 0.5N sulfuric acid. When no paraformaldehyde is present, the DCE was distilled at 40° C.-60° C. under reduced pressure. The temperature was then maintained at 60° C. for 30 minutes to ensure residual water and DCE are removed. The resultant residue containing ethyl 2-hydroxymethyl acrylate (EHMA) (27 kg) was analyzed for moisture content.

EHMA (27 kg, 207 moles) was charged to the reactor. HBr (48%, 3.25 eq, 112 kg, 672 mol) was added and the mixture was then cooled to 12° C. At 12° C., sulfuric acid (2.0 eq, 39 kg, 398 mol) was added at such a rate that the internal temperature did not exceed 15° C. After all the acid was added, the mixture was left to stir at room temperature (~22-26° C.) overnight. The reaction mixture was then extracted with hexane (3×33 kg). The hexane was pumped into the reactor, stirred for 30 minutes; allowed to settle for 30 minutes and then the phases separated. The hexane extract was washed with an aqueous sodium bicarbonate solution (5%, 33 kg). The mixture was stirred for 30 minutes, and then the stirrer stopped for 30 minutes to allow the phases to separate. This process was repeated twice. The washed hexane extract was then transferred to the distillation column. The hexane was then distilled at 40° C. under reduced pressure. The temperature was increased to 50° C. to remove any water that might be present. The residue containing EBMA was then distilled under high vacuum pump (80° C./<1 mm Hg) to obtain a 98% pure product (16.4 kg, 34%).

EXAMPLE 6

Laboratory Scale Production of Ethyl (Indolylmethyl)Acrylate Using ECMA

Magnesium turnings (228 mg, 1.1 eq) were covered with tetrahydrofuran (THF) (2 mL) under an atmosphere of nitrogen. A few drops of a solution of ethyl bromide (0.70 mL, 1.1 eq) in THF (2 mL) was then added without stirring in order to initiate the reaction. Once a vigorous reaction had begun, the remainder of the ethyl bromide solution was added dropwise and the reaction cooled as necessary to maintain the temperature below 35° C. with an ice bath. The reaction mixture was stirred for 30-40 min to allow for all of the magnesium to be consumed. Indole (1.0 g, 1.0 eq) was then added drop wise as a solution in THF (2 mL) with vigorous evolution of ethane gas, and with cooling in an ice-water bath as necessary. The resulting mixture was stirred for a further 30 min. The mixture was then cooled to −10° C., and a solution of ECMA (1.49 g, 1.0 eq, 85% purity) in THF (2 mL) was added to the cooled solution over a period of 2 min. The reaction mixture was allowed to warm to room temperature, and left to stir at this temperature for a further 30 min. The reaction was quenched by addition of water (10 mL) (exothermic), and the two phases separated. The aqueous phase was extracted with ethyl acetate (3×10 mL) and the organic extracts combined, dried (MgSO$_4$) and concentrated under reduced pressure. The crude product was analyzed by $^1$H NMR spectroscopy and shown to contain the desired product in approximately 80% purity.

EXAMPLE 7

The (indolylmethyl)acrylate ester, such as ethyl 2-(indolylmethyl)acrylate (EIMA), was prepared by the reaction of indolemagnesium bromide with a bromomethyl acrylate ester such as EBMA. Alternatively, a chloromethyl acrylate ester may also be used, although in most cases EBMA was used. The nature of the ester produced is dependent on the acrylate starting material used in the preparation of the bromomethyl or chloromethyl acrylate ester, such as methyl or ethyl acrylate, however in most cases ethyl acrylate was used. The Grignard reagent (such as methylmagnesium chloride or ethylmagnesium bromide) used to generate indolemagnesium chloride or bromide may be either generated from magnesium turnings and ethyl chloride or bromide or be purchased as a solution in THF or diethyl ether.

The reaction is moisture sensitive and was carried out under anhydrous conditions using an inert gas such as nitrogen or argon. However, trace quantities of water (<0.03% m/m) did not have a detrimental effect on the reaction performance and pre-drying of the solvent (such as THF or diethyl ether) by distillation from sodium was not required for the large scale synthesis.

During the course of the investigation it was observed that in addition to the formation of the desired product, other complex indole/acrylate adducts were produced, and several experiments were conducted in an attempt to minimize by-product formation, including changing the mode and order of addition of reagents, and also by adding bases or chelating agents such as triethylamine or magnesium oxide to effectively avoid reaction at the nucleophilic indole nitrogen. However, either no reduction in by-product formation was observed, or a lower conversion to product was observed.

The purity of EBMA starting material has a significant effect on the performance of the Grignard reaction. When EBMA of purity <90% was used, a significant decrease in conversion of indole was noted, possibly due to quenching of the Grignard reagent by impurities present. This resulted in additional molar equivalents of Grignard reagent required for reaction, and an overall decrease in yield of product of approximately 10%.

On laboratory scale (and described in U.S. Pat. No. 5,128,482), the crude EIMA isolated from the reaction mixture was purified by silica gel column chromatography, which would not be feasible for large scale purification. In general, alternative methods of purification include selective liquid-liquid extraction, crystallization for products that are solids, or distillation for volatile oils. Selective extraction was not possible as a method of purification in this case as the product and by-products were very closely related and displayed similar solubilities in organic solvents. Crystallization was not considered to be a feasible method of purification because EIMA was never isolated as a solid, although the related methyl ester (methyl 2-(indolylmethyl)acrylate) was found to be a waxy solid in pure form. This was surprising as compounds containing an unprotected indole moiety are often isolated as crystalline solids. In addition, attempts to purify the methyl ester (methyl 2-(indolylmethyl)acrylate) by crystallization failed. Although distillation was considered to be an unlikely method of purification for this non-volatile viscous oil, it was attempted on a small scale and shown to be possible in principle. However, when the classical distillation was repeated on 2 L scale, significant decomposition of the product was observed. An alternative wiped-film short path distillation (SPD) was attempted using the parameters defined in the Table below, which minimizes the time that the product is exposed to high temperatures. This was found to successfully separate the product from the high boiling by-products, and afforded the desired product at a purity of 70-75% by % m/m.

TABLE

| Short path distillation unit process parameters | |
|---|---|
| Conditions | Process parameters |
| Feed temperature (° C.) | 90 |
| Condenser temperature (° C.) | 60 |
| Column temperature (° C.) | 170-190 |
| Vacuum (mbar) | 0.15-0.7 |
| Flow rate (ml/hour) | 140-300 |
| Distillate:re-boiler ratio | 1.7-2.5:1 |

Further purification of this mixture by vigreux distillation on <1 L scale to allow for fractional purification of the product afforded the desired product in high purity (>90%), but very low yield (<28%). Scaling this distillation up resulted in further reduction in yields to <15% as extended heating times were required and this resulted in significant product decomposition (>50%).

As an alternative, the material after SPD, which was only 70% pure, was tested in the subsequent cycloaddition reaction with ethyl chlorohydroxyiminoacetate (ECHA) to afford the isoxazoline diethyl ester (ID). The results obtained showed that EIMA of purity >70% could be used successfully in the cycloaddition step without additional purification. In this way, we were able to overcome the complex issue of complete purification of EIMA on a large scale. Using this downstream processing protocol for EIMA preparation, the yield of product on 15 L scale ranged from 45-54%, with the average yield over 10 runs being 49%. This is comparable with the yield described in U.S. Pat. No. 5,128,482, (47%) and only slightly lower than the yields obtained in our laboratory investigations (55-65%).

EXAMPLE 8

Preparation of EIMA Using EBMA

Magnesium turnings (13.36 g, 1.1 eq) were covered with tetrahydrofuran (THF) (125 mL) under an atmosphere of nitrogen. Approximately 2 mL of a solution of ethyl bromide (41.0 mL, 1.1 eq) in THF (125 mL) was then added dropwise without stirring in order to initiate the reaction. Once a vigorous reaction had begun, the remainder of the ethyl bromide solution was added dropwise and the reaction cooled as necessary to maintain the temperature below 35° C. with an ice bath. The reaction mixture was stirred for 30-40 min to allow for all of the magnesium to be consumed. Indole (58.5 g, 1.0 eq) was then added drop wise as a solution in THF (125 mL) with vigorous evolution of ethane gas, and with cooling in an ice-water bath as necessary. The resulting mixture was stirred for a further 30 min. The mixture was then cooled to −10° C., and a solution of ethyl 2-(bromomethyl)acrylate (104.0 g) (Example 1) in THF (125 mL) was added to the cooled solution over a period of 10 min. The reaction mixture was allowed to warm to room temperature, and left to stir at this temperature for a further 30 min. The reaction was quenched by drop wise addition of water (200 mL) over 20 min (exothermic), and the two phases separated. The aqueous phase was extracted with ethyl acetate (300 mL) and the organic extracts combined, dried ($MgSO_4$) and concentrated under reduced pressure. The crude product was purified by silica gel column chromatography (500 g silica, 10% EtOAc-hexane as eluent) to afford the pure product as a pale yellow oil (75.5 g, 66%).

EXAMPLE 9

Laboratory Scale Production of EIMA Using Preformed Grignard Reagent

An indole/THF solution (33% m/m, 33 g, containing 10.9 g indole, 94.5 mmol) was charged to the reactor and cooled to between 0° C.-5° C. under a nitrogen atmosphere. The preformed Grignard reagent (methyl magnesium chloride, 22% m/m, 34.5 g, 102.5 mmol) was then added drop-wise over 10-30 minutes while ensuring that the reaction temperature did not exceed 30° C. The reaction mixture was then stirred for a further 45 minutes. A solution of ethyl 2-(bromomethyl) acrylate (EBMA)/THF (48% m/m, 42 g, 103.6 mmol) was added drop-wise over 15-30 minutes, while ensuring that the reaction temperature did not exceed 5° C. (−10° C. to 5° C.) and maintained under these reaction conditions for a further 1 hour.

The reaction mixture was then quenched with water (40 $cm^3$) while ensuring that the reaction temperature did not exceed 30° C. to 35° C. The organic and aqueous phases were separated. Due to the miscibility of THF in water, the aqueous phase was extracted twice with ethyl acetate (2×100 $cm^3$). The organic fractions (THF/ethyl acetate) were combined and concentrated at 40° C. to 90° C. under vacuum (5-10 mbar). The residue was purified by column chromatography (hexane:ethyl acetate 9:1) to afford EIMA (13.7 g, 64%).

EXAMPLE 10

Bench Scale Production of EIMA

An indole/THF solution (5.88 kg, 34% m/m, containing 2 kg indole, 17.1 moles) was charged to the reactor and cooled to 0° C. under an atmosphere of nitrogen. The Grignard reagent (6.32 kg, 22% m/m, containing, 1.39 kg methyl magnesium chloride, 18.8 moles) was charged over 105 minutes and the reactor temperature maintained between 6° C. and 10° C. The reaction mixture was stirred for a further 30 minutes under the above reaction conditions. An EBMA/THF solution (6.87 kg, 46% m/m, 17.1 moles) was then added over 120 minutes while maintaining the reaction temperature between 3° C. and 5.0° C., and stirred for an additional 60 minutes. The reaction mixture was then quenched with water (7.5 kg) and heated to ~20° C. in order to dissolve salts. The aqueous and organic phases were separated, and the aqueous phase was extracted twice with ethyl acetate (7.5 kg, 10.5 kg). The ethyl acetate/THF phases were combined and concentrated under vacuum of 5-10 mbar at 40-90° C. The organic residue was passed through a short path distillation unit to facilitate removal of high boiling components under the following conditions specified in the table entitled "Short path distillation unit process parameters", above.

The distillate (2.38 kg) contained 76.8% m/m EIMA as validated HPLC analysis (46.5% yield).

EXAMPLE 11

Laboratory-Scale Production of ECHA

Ethyl chlorohydroxyiminoacetate (ECHA) can be produced from glycine ethyl ester hydrochloride by the in-situ generation of nitrosyl chloride gas from aqueous sodium nitrite and HCl. In particular, Glycine ethyl ester.HCl is dissolved in water. To this is added concentrated HCl solution (32%) and the reaction mixture is cooled to <10° C. HCl gas is then bubbled into the reaction mixture. An aqueous solution of sodium nitrite is dosed into the reactor while maintaining the temperature at <10° C. HCl gas is bubbled into the reactor again followed by a second portion of aqueous sodium nitrite. Finally, the product is purified from the reaction mixture by any appropriate means known to those of skill in the art. For example, the reaction mixture is stirred for a further period and then extracted with a water immiscible solvent (dichloroethane, chloroform, carbon tetrachloride) at room temperature to remove the product from the reaction mixture. The organic extracts are dried with a drying agent and the solvent is flashed off. An oily residue remains, which crystallizes on cooling. The crystals are filtered and washed with a suitable solvent to obtain a purified ECHA.

EXAMPLE 12

Large-Scale Production of ECHA

Glycine ethyl ester hydrochloride (6.3 kg, 0.045 kmol) was dissolved in hydrochloric acid (32%, 5.13 kg). The solution was cooled to 0° C. and hydrochloric acid gas was bubbled into the reactor via a sparging tube for 1 hour while maintaining the temperature at <5° C. The reaction mixture was then cooled to −5° C. A solution of sodium nitrite (3.11 kg) in water (4.5 L) was then dosed into the reactor using a diaphragm pump while maintaining the temperature at −5° C. to 0° C. This operation was complete within an hour. A second portion of gaseous HCl was sparged into the reactor over 1 hour at 0 to 5° C. This was followed by a second portion of sodium nitrite (3.11 kg) in water (4.5 L) which was added over one hour while maintaining the temperature at −5° C. to 0° C. The reaction mixture was stirred for a further hour and was then extracted with chloroform (3×2 kg) at ambient temperature. The organic extracts were combined, dried ($MgSO_4$) and evaporated in-vacuo (40° C.). An oily residue remained which crystallized upon cooling to ambient temperature. The crystals were filtered and washed with hexane (2 kg) at 5° C. The crystals were dried under vacuum to obtain a pure (by NMR), white product (2.53 kg, 36.9%). The yield of ECHA over 10 runs ranged from 31.4 to 51.2% at an average of 39.8%.

EXAMPLE 13

Laboratory-Scale Preparation of ECHA

Reactions were carried out in a 1 L, jacketed, baffled reactor equipped with an overhead mechanical propeller-type stirrer and a sparging tube positioned below the surface of the reaction mixture. Glycine ethyl ester hydrochloride (210 g, 1.50 moles) was dissolved in water (270 mL) and added to the reactor. To this was added hydrochloric acid (32%, 54.7 g, 1.52 moles). The solution was cooled to 0° C. and hydrochloric acid gas was bubbled for 30 minutes into the reactor via the sparging tube. The gas was generated by adding aqueous hydrochloric acid (32%, 100 mL) to concentrated sulfuric acid (98%, 100 mL) using a dropping funnel while maintaining the temperature of the acid mixture at less than 5° C. The reaction mixture was then cooled to −5° C. A solution of sodium nitrite (103.5 g, 1.50 moles) in water (150 mL) was then dosed into the reactor using a diaphragm pump while maintaining the temperature at −5° C. to 0° C. This operation was complete within an hour. A second portion of gaseous HCl (ex. 100 mL HCl and 100 mL $H_2SO_4$) was sparged into the reactor over 30 minutes at 0 to 5° C. This was followed by a second portion of sodium nitrite (103.5 g, 1.50 moles) in water (150 mL) which was added over one hour while maintaining the temperature at −5° C. to 0° C. The reaction mixture was stirred for a further 30 minutes and was then extracted with chloroform (3×200 mL) at ambient temperature. The organic extracts were combined, dried ($MgSO_4$) and evaporated in-vacuo (40° C.). An oily residue remained which crystallized upon cooling to ambient temperature. The crystals (192.4 g) were stirred with hexane (200 mL) at 5° C. for 1 hour and then filtered. The crystals were dried under vacuum to afford the ethyl chlorohydroxyiminoacetate product (122.1 g, 0.81 moles, 53.9%).

EXAMPLE 14

Preparation of Isoxazoline Diester

Ethyl (indolyl methyl)acrylate (57.3 g) (Example 2) was dissolved in chloroform (675 mL) and treated with triethylamine (50.6 g, 2.0 eq). ECHA (45.5 g, 1.2 eq) (Examples 11-13) in chloroform (555 mL) was added dropwise over 2 hours at room temperature. After this time LC analysis showed that the reaction was complete, and the mixture was then quenched with water (400 mL). The phases were separated and the organic phase was washed with water (2×400 mL). The organic phase was dried ($MgSO_4$) and concentrated under reduced pressure. Crystallization of the product was facilitated by addition of ethanol (100 mL) and water (20 mL). The precipitate was filtered and dried under vacuum to afford the product (62.2 g, 72%). This product was thus isoxazoline diester, i.e., the compound of formula (VI).

EXAMPLE 15

Reduction of Isoxazoline Diester and Isolation of RR/SS and RS/SR Monatin

Sponge Nickel Catalyst

The reaction was carried out in the 1 L Labmax® pressure reactor. Potassium hydroxide (33.9 g, 0.61 moles) was dissolved in 90% aqueous ethanol (400 mL). To this was added isoxazoline diester (50 g, 0.15 moles) (Example 14) and a sponge nickel catalyst (available under the designation A-7063 from Activated Metals Corporation, 50 g) as a wet paste containing about 50% water. The mixture was transferred to the reactor, which was then sealed and evacuated for 5 minutes while stirring at 300 rpm. The reaction mixture was cooled to 20° C. and hydrogen gas was fed into the reactor at a pressure of 5 bar. The reactor was left open to the cylinder for the duration of the reaction. The reaction was continued for 90 minutes under these conditions. The progress of the reaction was monitored by HPLC. On completion of the reaction, the reactor was drained and the catalyst was filtered through a celite bed on a Buchner funnel. The filtrate was then treated with an equivalent of glacial acetic acid (36.4 g, 0.61 moles).

Ethanol was removed under reduced pressure, and the reaction mixture was concentrated to a volume of approximately 100 mL. The mixture was left to stand overnight to allow RR/SS Monatin to precipitate out of the aqueous solution. The RR/SS Monatin isolated by filtration (15.8 g) was only 90% pure by LC, and was recrystallized by treatment with water (80 mL) and aqueous ammonia (8.4 mL) to a pH of 9.3. This was followed by acidification with 50% aqueous acetic acid (14.7 mL). This afforded RR/SS Monatin (12.1 g) at a purity of 94% as shown by LC.

Recrystallization was repeated to afford 11.8 g of 96% RR/SS Monatin. A further recrystallization with charcoal treatment (3% charcoal, 354 mg) afforded 10.6 g of RR/SS Monatin at a purity of 97.7%.

The mother liquor from the reaction was concentrated to a volume of 80 mL, and treated with ethanol (300 mL). RS/SR Monatin was left to precipitate out of solution overnight.

EXAMPLE 16

Reduction of Isoxazoline Diester

Rhodium/Carbon Catalyst

The isoxazoline diester (0.25 g) was added to an ethanol/water solution (9:1 ratio, 2.5 mL) of potassium hydroxide (0.16 g) at room temperature. Rhodium on carbon catalyst (5% on carbon, 0.25 g) was added and the system was charged to 5 bar pressure with hydrogen gas. The mixture was stirred under hydrogen at room temperature for 2 hours. HPLC analysis revealed a mixture of monatin isomers in 92% total yield with the RR/SS:RS/SR ratio 1.4:1.

EXAMPLE 17

Reduction of Isoxazoline Diester

Sponge Nickel Catalyst

The isoxazoline diester (0.25 g) was added to an ethanol/water solution (9:1 ratio, 2.5 mL) of potassium hydroxide (0.16 g) at room temperature. Nickel catalyst (A4000, water dispersion, 0.25 g) and copper chloride (50 mg) were added and the system was charged to 5 bar pressure with hydrogen gas. The mixture was stirred under hydrogen at room temperature for 2 hours. HPLC analysis revealed a mixture of monatin isomers in 86% total yield with the RR/SS:RS/SR ratio 1.2:1.

EXAMPLE 18

Reduction of Isoxazoline Diester

Sponge Nickel Catalyst

The isoxazoline diester (0.25 g) was added to an ethanol/water solution (9:1 ratio, 2.5 mL) of potassium hydroxide (0.16 g) at room temperature. Nickel catalyst (A4000, water dispersion, 0.25 g) and N-benzylcinchonidinium chloride (14 mg) were added and the system was charged to 5 bar pressure with hydrogen gas. The mixture was stirred under hydrogen at room temperature for 2 hours. HPLC analysis revealed a mixture of monatin isomers in 88% total yield with the RR/SS:RS/SR ratio 1.3:1.

EXAMPLE 19

Reduction of Isoxazoline Diester

Sponge Nickel Catalyst

The isoxazoline diester (0.25 g) was added to an ethanol/water solution (9:1 ratio, 2.5 mL) of potassium hydroxide (0.16 g) at room temperature. Nickel catalyst (A5200, water dispersion, 0.25 g) was added and the system was charged to 5-bar pressure with hydrogen gas. The mixture was stirred under hydrogen at room temperature for 2 hours. HPLC analysis revealed a mixture of monatin isomers in 92% total yield with the RR/SS:RS/SR ratio 1.1:1.

EXAMPLE 20

Reduction of Isoxazoline Diester

Sponge Nickel Catalyst

The isoxazoline diester (0.25 g) was added to an ethanol/water solution (9:1 ratio, 2.5 mL) of potassium hydroxide (0.16 g) at room temperature. Nickel catalyst (A7000, mineral oil dispersion, 0.25 g) and benzyltributylammonium chloride (0.25 g) were added and the system was charged to 5 bar pressure with hydrogen gas. The mixture was stirred under hydrogen at room temperature for 2 hours. HPLC analysis revealed a mixture of monatin isomers in 94% total yield with the RR/SS:RS/SR ratio 1:1.

EXAMPLE 21

Reduction of Isoxazoline Diester

Palladium Catalyst

The isoxazoline diester (0.25 g) was added to an ethanol/water solution (9:1 ratio, 2.5 mL) of potassium hydroxide (0.16 g) at room temperature. Palladium on carbon catalyst (5% on carbon, Johnson Matthey type 338, 0.25 g) was added and the system was charged to 5 bar pressure with hydrogen gas. The mixture was stirred under hydrogen at room temperature for 2 hours. HPLC analysis revealed a mixture of monatin isomers in 31% total yield with the RR/SS:RS/SR ratio 1.9:1.

EXAMPLE 22

Reduction of Isoxazoline Diester and Isolation of RR/SS and RS/SR Monatin

Sponge Nickel Catalyst

Potassium hydroxide (4.0 eq, 3 kg, 0.05 kmol) was charged to the reactor with ethanol (37 kg). The system was cooled to 21° C. and to this was added isoxazoline diester (4.6 kg, 0.013 kmol). The sponge nickel catalyst (A-7063, 4.6 kg approximately 50% wet) was added to the reactor with stirring (215 rpm) to minimize settling. The reactor was sealed and purged with nitrogen at 1 bar(g) for five minutes. The reactor was sealed and pressurized with nitrogen up to 1 bar(g) and the nitrogen supply isolated. Hydrogen was fed to the reactor so that the total pressure of the system was 2 bar(g). The reaction was run at this pressure for 30 minutes with the hydrogen supply line open. The conversion after 30 minutes was 71.6%. Hydrogen was then used to further pressurize the reactor to 3 bar(g) and the system maintained for 25 minutes. A conversion of 97.23% was obtained. The system was then pressurized to 5 bar(g) and run for 30 minutes to ensure complete conversion of the isoxazoline diester. After complete reaction, the reactor was vented and flushed with nitrogen (1 bar(g)) for 5 minutes, prior to being pressurized to 1.5 bar(g). The material was filtered through a Nutsche filter at this pressure. The catalyst bed was not filtered to dryness owing to the pyrophoric nature of the catalyst. The filtrate (46.1 kg) was then concentrated in a 40 L vessel equipped with a steam coil, condenser and receiving vessel. The final mass of the concentrate was 10.8 kg.

The concentrate was treated with water and glacial acetic acid in a 16 L glass-lined, stirred reactor at 20-25° C. The system was acidified with acetic acid to a pH of 4.5 and maintained at 20° C. for approximately 15 hours. The slurry was drained and centrifuged to isolate the solids. The solids obtained from the first precipitation were put to a subsequent precipitation. The solids were slurred in water and added to the reactor. Aqueous ammonium hydroxide solution was added to the system to adjust the pH to ~8.5. Acetic acid was added to acidify the system back to pH 4.5. The reactor was then cooled to approximately 20° C. and maintained for 2 hours. The slurry was drained and centrifuged. This afforded 1.42 kg (73%) of RR/SS monatin within specification (98% by HPLC).

EXAMPLE 23

Preparation of N-Benzoyl Monatin

RS/SR Monatin (2.6 g, 8.90 mmol) (Example 22) was dissolved in aqueous sodium hydroxide solution (1M solution) and benzoyl chloride (1.25 g, 8.90 mmol) and the balance of the sodium hydroxide solution (1M, 8.90 mL in total) were added in four equal portions at room temperature. The resultant mixture was stirred at room temperature for 2 hours. The pH of the solution was reduced to pH 2 with hydrochloric acid solution (1M), and the product was extracted into dichloromethane. The solvent was removed, generating the required N-Benzoyl Monatin with an isolated yield of 94%.

Although the present invention has been described with reference to certain embodiments, persons skilled in the art will recognize that changes may be made in form and detail without departing from the spirit and scope of the invention.

What we claim is:

1. A process comprising:
    reacting an alkyl 2-chloromethylacrylate with an indole substrate in the presence of a Grignard reagent to form a mixture containing an alkyl 2-indolylmethylacrylate in which the indole rings are substituted according to the indole substrate starting material; and
    distilling the mixture to produce a purified alkyl 2-indolylmethylacrylate.

2. The process according to claim 1, wherein the purified alkyl 2-indolylmethylacrylate is at least about 70% pure.

3. The process according to claim 2, wherein the purified alkyl 2-indolylmethylacrylate is at least about 90% pure.

4. The process according to claim 1, wherein the alkyl 2-indolylmethylacrylate is ethyl 2-indolylmethylacrylate, further comprising reacting the ethyl 2-indolylmethylacrylate with ethyl chlorohydroxyiminoacetate to form isoxazoline diethylester.

5. The process according to claim 4 further comprising producing monatin from the isoxazoline diethylester.

6. The process according to claim 5 wherein the step of producing monatin from the isoxazoline diethylester comprises subjecting the isoxazoline diethylester to hydrolysis.

7. The process according to claim 6 wherein the step of producing monatin from the isoxazoline diethylester further comprises subjecting the isoxazoline diethylester to hydrogenolysis.

8. The process according to claim 7, wherein the reactions of hydrolysis and hydrogenolysis occur in the same step.

9. The process according to claim 7, wherein the purified 2-indolylmethylacrylate is at least about 50% pure.

10. The process according to claim 7, wherein the purified 2-indolylmethylacrylate is at least about 70% pure.

11. The process according to claim 7, wherein the purified 2-indolylmethylacrylate is at least about 90% pure.

12. The process according to claim 1, wherein the purified alkyl 2-indolylmethylacrylate is at least about 50% pure.

* * * * *